(12) United States Patent
Lerner et al.

(10) Patent No.: US 9,381,281 B2
(45) Date of Patent: Jul. 5, 2016

(54) DRUG ELUTING MESH TO PREVENT INFECTION OF INDWELLING TRANSDERMAL DEVICES

(75) Inventors: Daniel Jeremy Lerner, Scarsdale, NY (US); William McJames, Hillsborough, NJ (US); Randy Mansfield, Jacksonville, FL (US); Robert S. White, Plymouth, MN (US)

(73) Assignee: TYRX, INC., Monmouth Junction, NJ (US)

( * ) Notice: Subject to any disclaimer, the term of this patent is extended or adjusted under 35 U.S.C. 154(b) by 19 days.

(21) Appl. No.: 14/233,856

(22) PCT Filed: Jul. 20, 2012

(86) PCT No.: PCT/US2012/047542
§ 371 (c)(1),
(2), (4) Date: Apr. 11, 2014

(87) PCT Pub. No.: WO2013/013123
PCT Pub. Date: Jan. 24, 2013

(65) Prior Publication Data
US 2014/0220098 A1    Aug. 7, 2014

Related U.S. Application Data

(60) Provisional application No. 61/509,843, filed on Jul. 20, 2011.

(51) Int. Cl.
| | | |
|---|---|---|
| A61L 31/16 | (2006.01) |
| A61L 31/00 | (2006.01) |
| A61L 31/10 | (2006.01) |
| A61L 31/14 | (2006.01) |
| A61K 31/496 | (2006.01) |
| A61K 31/65 | (2006.01) |
| A61P 31/04 | (2006.01) |
| A61L 31/06 | (2006.01) |

(52) U.S. Cl.
CPC .............. *A61L 31/16* (2013.01); *A61L 31/06* (2013.01); *A61L 31/10* (2013.01); *A61L 31/146* (2013.01); *A61L 31/148* (2013.01); *A61L 2300/406* (2013.01); *A61L 2300/604* (2013.01); *A61L 2300/606* (2013.01); *A61L 2420/06* (2013.01)

(58) Field of Classification Search
CPC ......... A61L 31/06; A61L 31/10; A61L 31/16; A61L 2300/406; A61L 2300/604; A61L 2300/606; A61L 2430/06; A61L 31/146; A61L 31/148; C08L 77/12
See application file for complete search history.

(56) References Cited

U.S. PATENT DOCUMENTS

| | | | |
|---|---|---|---|
| 8,591,531 B2 * | 11/2013 | Buevich et al. | 606/151 |
| 2007/0198040 A1 | 8/2007 | Buevich et al. | |
| 2008/0132922 A1 | 6/2008 | Buevich et al. | |
| 2008/0146869 A1 * | 6/2008 | Chow et al. | 600/37 |
| 2008/0187567 A1 * | 8/2008 | Kohn et al. | 424/422 |
| 2010/0168808 A1 | 7/2010 | Citron et al. | |
| 2012/0185004 A1 * | 7/2012 | McJames et al. | 607/3 |
| 2015/0086604 A1 * | 3/2015 | Buevich et al. | 424/426 |

OTHER PUBLICATIONS

International Search and Written Opinion dated Nov. 9, 2012 in International Patent Appl. No. PCT/US2012/047542.
European Examination Report dated Jan. 13, 2016 in connection with European Patent Application No. 12746171.3.
Written Opinion of the International Searching Authority in Connection With PCT/US2012/047542.

* cited by examiner

*Primary Examiner* — Abigail Fisher
(74) *Attorney, Agent, or Firm* — Sorell, Lenna & Schmidt, LLP (57) ABSTRACT

In some embodiments, a device (102) may include a mesh having at least one bioresorbable polymer coating. The coating may comprise at least one active agent which is eluted over time. The device (102) may at least partially cover at least a portion of an implanted transdermal medical device (100).

30 Claims, 2 Drawing Sheets

DRUG ELUTING MESH TO PREVENT INFECTION OF INDWELLING TRANSDERMAL DEVICES

CROSS-REFERENCE TO RELATED APPLICATIONS

This application is a national phase entry under 35 U.S.C. §371 of International Application No. PCT/US2012/047542, filed Jul. 20, 2012, which claims the benefit of the filing date of U.S. Provisional Patent Application No. 61/509,843, filed Jul. 20, 2011, the disclosure of which is hereby incorporated herein by reference.

BACKGROUND OF THE INVENTION

Several types of medical devices require long-term transdermal communication between the internal and external portions of the device. Examples of such devices include arteriovenous shunts, left ventricular assist devices, tissue expanders, and gastric lap bands. The transdermal portion of the device can be in the form of a catheter, a gas insufflation tube, or an electrical wire. These types of transdermal medical devices (hereinafter "TMDs") are susceptible to infection.

For example, a laparoscopic adjustable gastric band (hereinafter "LAGB") is an inflatable device that is placed around the top portion of the stomach via laparoscopic surgery and is often used to treat obesity. Most LAGBs have three portions including: (1) a gastric band; (2) an access (or injection) port; and (3) a connection tube, which allows for fluidic communication between the access port and the gastric band.

In a surgical procedure, the LAGB is placed around the upper part of the stomach, creating a small pouch that can hold only a small amount of food. The narrowed opening between the stomach pouch and the rest of the stomach controls how quickly food passes from the pouch to the lower part of the stomach. Depending on the patient's needs, after the device is implanted the narrowed opening between the pouch and the lower part of the stomach can be adjusted in size by inflating or deflating the gastric band portion. Inflating the band makes the opening smaller, causing food to pass more slowly. Deflating the band makes it wider, causes food to pass more quickly.

The adjustment is made by adding or removing fluid inside the hollow gastric band portion, by injecting or removing the fluid through the access port. This access port is placed under the skin in a muscle in the chest wall. As such, the port area is in transdermal communication with an outside environment and may be susceptible to infection.

There remains a need to reduce the incidence of infection associated with TMDs.

SUMMARY OF THE INVENTION

In one aspect of the present invention is a mesh comprising at least one active pharmaceutical ingredient, wherein the active pharmaceutical ingredient is eluted from the mesh to an area adjacent an indwelling transdermal medical device. In one embodiment, the active pharmaceutical ingredient is an antimicrobial agent. In another embodiment, the mesh covers at least a portion of the transdermal medical device. In another embodiment, the mesh is placed adjacent to a transdermal medical device. In another embodiment, the mesh is placed between a transdermal medical device and a tissue susceptible to infection. In another embodiment, the active pharmaceutical ingredient is coated onto at least one surface of the mesh. In another embodiment, the mesh is secured to the transdermal medical device or to tissue by sutures, staples, clips, and adhesives. In another embodiment, the transdermal medical device is a laparoscopic adjustable gastric band.

In another aspect of the present invention is a gel comprising at least one active pharmaceutical ingredient, wherein the active pharmaceutical ingredient is eluted from the gel to an area adjacent to an indwelling transdermal medical device. In one embodiment, the gel is a polymer, pre-polymer, or hydrogel. In another embodiment, the active pharmaceutical ingredient is an antimicrobial agent. In another embodiment, the gel covers at least a portion of a transdermal medical device. In another embodiment, the gel is placed adjacent to a transdermal medical device. In another embodiment, the gel is placed between a transdermal medical device and a tissue susceptible to infection. In another embodiment, the transdermal medical device is a laparoscopic adjustable gastric band.

Without wishing to be bound by any particular theory, it is believed that by eluting an antimicrobial agent over time to an area surrounding a transdermal medical device, the incidence of microbial infections may be reduced, especially as the transdermal medical device is repeatedly accessed during medical treatment.

In some embodiments, a device may include a mesh having at least one bioresorbable polymer coating. The coating may comprise at least one active agent which is eluted over time. The device may at least partially cover at least a portion of an implanted transdermal medical device.

In some embodiments, the implanted transdermal medical device may be an indwelling medical device.

In some embodiments, the device may be porous.

In some embodiments, the device may be formed from knitted, braided, woven or non-woven fibers.

In some embodiments, the mesh may be formed of at least one bioresorbable polymer.

In some embodiments, the at least one bioresorbable polymer coating may be a tyrosine-derived polyesteramide.

In some embodiments, the tyrosine-derived polyesteramide may be a member of the P22 family of tyrosine-derived polyesteramides.

In some embodiments, a percentage of free acid in the P22 family of tyrosine-derived polyesteramides may range from about 5% to about 40%.

In some embodiments, a percentage of free acid in the P22 family of tyrosine-derived polyesteramide may be about 27.5%.

In some embodiments, the coating may comprise a tyrosine-derived polyesteramide and at least one polymer selected from the group consisting of polylactic acid, polyglycolic acid, poly(L-lactide) (PLLA), poly(D,L-lactide) (PLA) polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, polyethyl glutamate-co-glutamic acid), poly(tert-butyloxy-carbonylmethyl glutamate), polycaprolactone (PCL), polycaprolactone co-butylacrylate, polyhydroxybutyrate (PHBT), polyhydroxybutyrate, poly (phosphazene), poly(phosphate ester), poly(amino acid), polydepsipeptides, polyiminocarbonates, poly[(97.5% dimethyl-trimethylene carbonate)-co-(2.5% trimethylene carbonate)], poly(orthoesters), tyrosine-derived polycarbonates, tyrosine-derived polyiminocarbonates, tyrosine-derived polyphosphonates, polyethylene oxide, polyalkylene oxides, and hydroxypropylmethylcellulose.

In some embodiments, the active agent may be an antimicrobial agent, an anesthetic, a procoagulant agent, or an antiinflamatory agent.

In some embodiments, the antimicrobial agent may be selected from the group consisting of antibiotics, antiseptics, and disinfectants.

In some embodiments, the antibiotic may be selected from the group consisting of tetracyclines, penicillins, macrolides, rifampin and combinations thereof.

In some embodiments, the antibiotic may comprise a combination of minocycline and rifampin.

In some embodiments, the active agent may release from the coating over about a 24 hour time period.

In some embodiments, the active agent may release from the coating over about a 48 hour time period.

In some embodiments, the active agent may release from the coating over about a 120 hour time period.

In some embodiments, the active agent may be rifampin, minocycline, or a mixture thereof and wherein at least about 60% of said rifampin, minocycline, or a mixture thereof may be released within about 24 to about 36 hours.

In some embodiments, the active agent may be minocycline and a tissue concentration of the minocycline may be selected from the group consisting of between about 0.65 µg/mL and 0.8 µg/mL after about 2 hours, about 2.55 µg/mL and about 2.75 µg/mL after about 6 hours, and about 1.2 µg/mL and about 1.9 µg/mL after about 24 hours.

In some embodiments, the active agent may be minocycline and a tissue concentration of the minocycline may be between about 0.65 µg/mL and about 0.8 µg/mL after about 2 hours; where the tissue concentration of said minocycline is between about 2.55 µg/mL and about 2.75 µg/mL after about 6 hours; and where the tissue concentration of the minocycline may be between about 1.2 µg/mL and about 1.9 µg/mL after about 24 hours.

In some embodiments, a serum concentration may be less than about 0.1 µg/mL.

In some embodiments, the active agent may be rifampin and a tissue concentration of the rifampin may be selected from the group consisting of between about 0.6 µg/mL and 1.4 µg/mL after about 2 hours, about 1.9 µg/mL and about 2.3 µg/mL after about 6 hours, and about 2.6 µg/mL and about 4.2 µg/mL after about 24 hours.

In some embodiments, the active agent may be rifampin and a tissue concentration of the rifampin may be between about 0.6 µg/mL and 1.4 µg/mL after about 2 hours; where the tissue concentration of said rifampin is between about 1.9 µg/mL and about 2.3 µg/mL after about 6 hours; and where the tissue concentration of the rifampin may be between about 2.6 µg/mL and about 4.2 µg/mL after about 24 hours.

In some embodiments, the active agent may achieve a level equal or exceeding a minimum inhibitory concentration of said antibiotic for methicillin-resistant *Staphylococcus aureus* on both sides of said cardiovascular implantable electronic device for at least about 24 hours after implantation of the implanted transdermal medical device.

In some embodiments, the active agent may achieve a level equal or exceeding a minimum inhibitory concentration of said antibiotic for methicillin-resistant *Staphylococcus aureus* on both sides of the cardiovascular implantable electronic device for at least about 48 hours after implantation of the implanted transdermal medical device.

In some embodiments, a composition may comprise at least one bioresorbable polymer. The composition may comprise at least one active agent which may be eluted over time. The composition may at least partially cover at least a portion of an indwelling medical device.

In some embodiments, the composition may be a formulation selected from the group consisting of a putty, a paste, a gel, a foam, an ointment, and a cream.

In some embodiments, an amount of the at least one bioresorbable polymer may range from about 30% to about 80% by weight of the composition.

In some embodiments, the at least one bioresorbable polymer may be a tyrosine-derived polyesteramide.

In some embodiments, a method of reducing infection in tissue surrounding an implanted transdermal medical device may include eluting an active agent over time to the surrounding tissue. The active agent may be eluted from a composition or a device at least partially covering at least a portion of an indwelling medical device.

In some embodiments, the implanted transdermal medical device may be a laparoscopic adjustable gastric band.

In some embodiments, the active agent may be an antimicrobial agent, an anesthetic, a procoagulant agent, or an antiinflamatory agent.

In some embodiments, the mesh may prevent tissue ingrowth from a tissue surrounding the implanted transdermal device.

In some embodiments, the indwelling medical device may be selected from the group consisting of arteriovenous shunts, left ventricular assist devices, tissue expanders, gastric lap bands, spinal cord stimulators, intrathecal infusion pumps, deep brain stimulators, gastric electrical stimulators, sacral nerve stimulators, and vagus nerve stimulators.

DETAILED DESCRIPTION

The present invention is directed to a mesh or gel which at least partially covers, contacts, or is placed adjacent to a TMD, including a LAGB. The mesh or gel further comprises at least one active pharmaceutical ingredient (API), such as an antimicrobial agent, which eluted into the surrounding tissue over time.

As used herein, the term "mesh" refers to a mesh, pouch, bag, covering, shell, skin or receptacle comprised of a solid or semi-solid material.

As used herein, the term "gel" refers to a formulation or composition which is sufficiently viscous to remain in place.

As used herein, the term "transdermal medical device" ("TMD") refers to any indwelling medical device ("IMD") which is routinely accessed transdermally, or includes a transdermal component, and includes arteriovenous shunts, left ventricular assist devices, tissue expanders, gastric lap bands, spinal cord stimulators, intrathecal infusion pumps, deep brain stimulators, gastric electrical stimulators, sacral nerve stimulators, and vagus nerve stimulators. Gastric bands are available from Allergan, Inc. and sold under the brand-name LAP-BAND®. Gastric bands are also available from Ethicon, Inc. and sold under the brand-name Realize®. Gastric bands are also available from Helioscopie (France) and Midband (Dardilly, France).

The mesh or gel of the present invention may be utilized in combination with techniques such as vein harvesting, rotator cuff repair, cranioplasty, or craniotomy.

For example, vein harvesting is a technique used by cardiothoracic surgeons in coronary artery bypass graft surgery (CABG). Harvested vein/artery is used to bypass a blocked artery near the heart. The saphenous vein and the radial artery are the most common vessels used. Infection rates of between <1% for deep infection and between 4 and 5% for superficial infections have been reported *Staphylococcus aureus Staphylococcus epidermidis, Enterococcus, Streptococcus* are among the most common causative bacteria. While IV Prophylactic antibiotics like Cefuroxime, Cefamandole, Cefazolin, and Vancomycin are commonly used, no site specific antibiotics or prostheses are employed in current vein harvesting techniques.

Similarly, infection rates are about 2 to about 5% from Cranioplasty, and up to about 8% for Craniotomy.

For example, rotator cuff repair is technique used by orthopedic surgeons to repair and reattach the tendon back to the bone. Types of rotator cuff repair techniques can include arthroscopic repair, mini-open repair, and open surgical repair. Bacteria such as *Staphylococcus epidermis, Staphylococcus aureus*, and *Propionibacterium acnes* can be responsible for infections in rotator cuff repair. The infection rates in primary procedures are less than 2%. However, failure rates for primary procedures can be very high, necessitating revisions and the infection rates associated with are significantly higher about 10%.

The mesh or gel of the present invention may be implanted contemporaneously with the TMD or after surgical implantation of the TMD. For example, a mesh may be secured to the port of a LAGB prior to surgical implantation of the LAGB. Or, for example, the port of the LAGB may be implanted first followed by implanting of a mesh or instilling a formulation/composition around at least a portion of the port.

Mesh Devices

In some embodiments, the mesh is comprised of a permanent or bioresorbable material and may be porous or nonporous. The materials comprising the mesh are known to those of ordinary skill in the art. In some embodiments, the mesh may comprise one or more terpolymers of glycolide, caprolactone, and trimethylene carbonate. In some embodiments, the mesh may include terpolymer of glycolic 6-hydroxycaproic acid and 1-3 propanediol.

The mesh may be of any shape or size. The mesh may be shaped to encapsulate, encase, surround, cover or hold at least a portion of a TMD, an IMD or LAGB. In some embodiments, the mesh is secured to tissue in an area adjacent to the TMD or LAGB or between the TMD and a tissue, such as a tissue susceptible to infection. For example, the mesh may be secured between the epidermis or muscle wall and the access port of a LAGB. The mesh is held in place with sutures, staples, clips, adhesives, or by another other attachment method known to those of skill in the art.

A mesh in accordance with the invention is any web or fabric with a construction of knitted, braided, woven or non-woven filaments or fibers that are interlocked in such a way to create a fabric or a fabric-like material. As used in accordance with the present invention, "mesh" also includes any porous prosthesis suitable for surrounding, covering, holding, or encapsulating a TMD or an IMD.

In some embodiments, the mesh may have a burst load ranging from about 150 to about 450 N. In some embodiments, the mesh may have a break strength ranging from about 20 to about 80 N. In some embodiments, the mesh may have a break elongation ranging from about 45 to about 300%. In some embodiments, the mesh may have a filament denier ranging from about 80 to about 300 g/9000 m. In some embodiments, the mesh may have an areal density ranging from about 30 to about 150 g/m$^2$. In some embodiments, the mesh may have a thickness ranging from about 0.14 to about 0.50 millimeters.

Meshes can have one or more coatings, including polymer coatings, and include at least one API in at least one of the coatings. The API may be coated onto the surface of the mesh or be present in a matrix, such as with a bioresorbable polymer. As such, the release of the API from the mesh may be controlled. It is believed that meshes with at least a single coating are useful in improving handling of the mesh during surgical implantation and use. Meshes with APIs may be coated with single or multiple layers, depending on the amount of API to be delivered, the type of API and desired release rate. Each layer can contain the same or different polymers, the same or different APIs, and the same or different amounts of polymers or APIs. For example, a first coating layer can contain an API, while the second layer coating layer contains either no API or a lower concentration of API.

In some embodiments, the coatings on the meshes of the invention are formed from biodegradable polymeric layers that optionally contain one or more APIs. Methods of making biodegradable polymers or polymer coatings are well known in the art.

The polymers and biodegradable polymers suitable for use in the invention include but are not limited to: polylactic acid, polyglycolic acid and copolymers and mixtures thereof such as poly(L-lactide) (PLLA), poly(D,L-lactide) (PLA), polyglycolic acid[polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly (glycolide-co-trimethylene carbonate) (PGA/PTMC), poly (D,L-lactide-co-caprolactone) (PLA/PCL) and poly (glycolide-co-caprolactone) (PGA/PCL); polyethylene oxide (PEO), polydioxanone (PDS), polypropylene fumarate, poly (ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

In some embodiments, biodegradable polymers of the invention have diphenol monomer units that are copolymerized with an appropriate chemical moiety to form a polyarylate, a polycarbonate, a polyiminocarbonate, a polyphosphonate or any other polymer.

In some embodiments, the biodegradable polymers are tyrosine-based polyarylates including those described in U.S. Pat. Nos. 4,980,449; 5,099,060; 5,216,115; 5,317,077; 5,587, 507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337. These patents and publications also disclose other polymers containing tyrosine-derived diphenol monomer units or other diphenol monomer units, including polyarylates, polycarbonates, polyiminocarbonates, polythiocarbonates, polyphosphonates and polyethers.

Likewise, the foregoing patents and publications describe methods for making these polymers, some methods of which may be applicable to synthesizing other biodegradable polymers. Finally, the foregoing patents and publications also describe blends and copolymers with polyalkylene oxides, including polyethylene glycol (PEG). All such polymers are contemplated for use in the present invention.

The representative structures for the foregoing polymers are provide in the above-cited patents and publications which are incorporated herein by reference.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

Additional preferred polyarylates are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used informing the polyarylates) include succinate, glutarate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

The most preferred polyarylates are the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT.

Additionally, the polyarylate polymers used in the present invention can have from 0.1-99.9% PEG diacid to promote the degradation process as described in U.S. provisional application Ser. No. 60/733,988. Blends of polyarylates or other biodegradable polymers with polyarylates are also preferred.

Methods of coating the mesh with a polymer and/or API are disclosed in U.S. Patent Publication No. 2008/0132922, the disclosure is hereby incorporated by reference herein.

Figure 1:
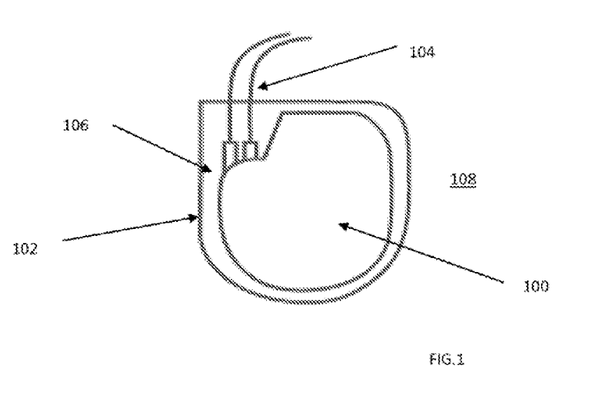
FIG. 1 depicts a schematic view of a device having a mesh and implantable transdermal device in accordance with some embodiments of the present invention.
Figure 2:
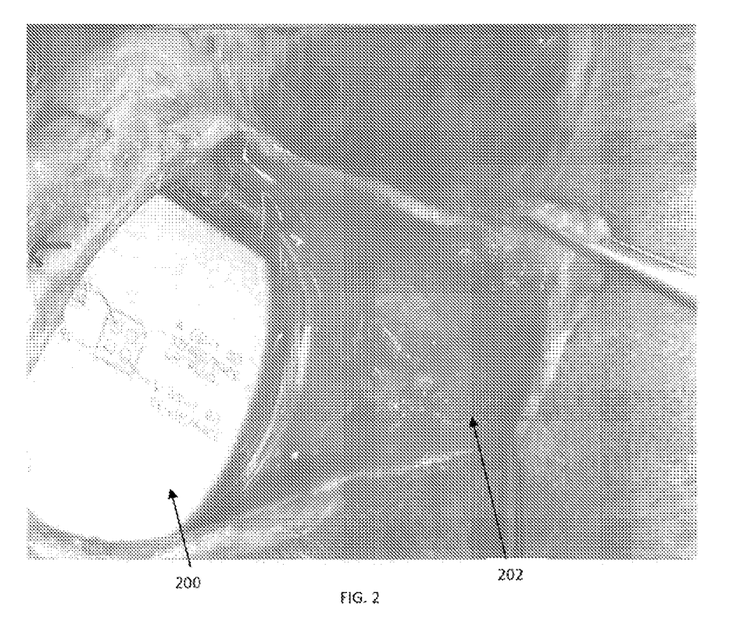
FIG. 2 depicts a dissected view of a test animal having an implantable transdermal device at least partially covered by a device having a mesh in accordance with some embodiments of the present invention.

FIG. 1 depicts an exemplary schematic view of a device having a mesh at least partially surrounding a TMD in accordance with some embodiments of the present invention. As shown, an exemplary TMD or IMD 100 may be at least partially covered by a device 102 having a mesh. The exemplary TMD 100 may include one or more of a cardiovascular implantable electronic device, an implantable infusion device, an implantable non-cardiac pulse generator, a implantable physiological monitoring device, or other types of TMDs. The TMD 100 may include one or more components 104 which may extend from an internal portion 106 of the device 102 to a surrounding environment 108 which surrounds the device 102. Exemplary components 104 may include one or more of leads, adapters, extensions or the like. An exemplary external environment may include tissues of a body. The mesh of the device 102 surrounding the TMD 100 device may serve as a barrier preventing the surrounding environment 108, such as a tissue of a body, from growing into the internal portion of the device 102. Thereby, the tissue may be prevented from becoming intertwined with the TMD 100. For example, FIG. 2 depicts a dissected view of a test animal having an implantable transdermal device 200 at least partially covered by a device having a mesh in accordance with some embodiments of the present invention. As shown in FIG. 2, the surrounding tissue 202 proximate the TMD 200 is not intertwined with the TMD 200.

Gel Devices

In some embodiments, a gel composition or formulation is applied to an area which at least partially surrounds or covers at least a portion of a TMD, an IMD or LAGB. In other embodiments, a gel composition or formulation is applied adjacent to an area surrounding a TMD, an IMD or LAGB. The formulation may be made of any appropriate material and are generally formulated as a gel, viscous fluid, paste, putty, cream, ointment, or foam. The formulation is sufficiently viscous to remain in place and elute API over time.

In some embodiments, the formulation or composition comprises a polymeric material (or polymeric precursor which forms a polymer, gel, hydrogel, or viscous fluid in situ) and at least one API. In other embodiments, the formulation comprises a tyrosine-derivative polyesteramide and at least one API and as described in copending U.S. patent application Ser. No. 12/791,586, the disclosure of which is hereby incorporated by reference herein.

In some embodiments, compositions of the invention include a tyrosine-derived polyesteramide and at least one additional polymer selected from the group consisting of polylactic acid, polyglycolic acid, poly(L-lactide) (PLLA), poly(D,L-lactide) (PLA) polyglycolic acid [polyglycolide (PGA)], poly(L-lactide-co-D,L-lactide) (PLLA/PLA), poly(L-lactide-coglycolide) (PLLA/PGA), poly(D, L-lactide-coglycolide) (PLA/PGA), poly(glycolide-cotrimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone cobutylacrylate, polyhydroxybutyrate (PHBT), polyhydroxybutyrate, poly(phosphazene), poly(phosphate ester), poly (amino acid), polydepsipeptides, polyiminocarbonates, poly

[(97.5% dimethyl-trimethylene carbonate)-co-(2.5% trimethylene carbonate)], poly(orthoesters), tyrosine-derived polycarbonates, tyrosine-derived polyiminocarbonates, tyrosine-derived polyphosphonates, polyethylene oxide, polyalkylene oxides, and hydroxypropylmethylcellulose.

In some embodiments of the method, the composition further includes a binder, for example polyethylene glycol (PEG). In particular embodiments, the PEG is PEG 400. In other embodiments of the method, the composition further includes an osteoinductive agent. In other embodiments of the method, the composition further includes an osteoconductive agent.

Active Pharmaceutical Ingredients

The mesh or gel of the present is designed to elute an API over time.

Any API (including biological agents) which compatible with the mesh or composition/formulation may be included. Doses of such APIs and agents are known in the art and those of skill in the art can readily determine the amount of a particular drug to include in the coatings on the meshes of the invention.

Examples of APIs suitable for use with the present invention include anesthetics, antibiotics (antimicrobials), anti-inflammatory agents, procoagulant agents, fibrosis-inhibiting agents, anti-scarring agents, leukotriene inhibitors/antagonists, cell growth inhibitors and the like. As used herein, API is used to include all types of therapeutic agents, whether small molecules or large molecules such as proteins, nucleic acids and the like. The APIs of the invention can be used alone or in combination.

Any pharmaceutically acceptable form of the APIs of the present invention can be employed in the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antimicrobials include, but are not limited to, triclosan, chlorhexidine, rifampin, minocycline (or other tetracycline derivatives), vancomycin, gentamycine, cephalosporins and the like. In preferred embodiments the coatings contain rifampin and another antimicrobial agent, preferably that agent is a tetracycline derivative. In another preferred embodiment, the coatings contains a cephalosporin and another antimicrobial agent. Preferred combinations include rifampin and minocycline, rifampin and gentamycin, and rifampin and minocycline.

Further antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other APIs that can be incorporated into the coatings on the mesh pouches of the invention include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

Additional, APIs include those that act as angiogenensis inhibitors or inhibit cell growth such as epidermal growth factor, PDGF, VEGF, FGF (fibroblast growth factor) and the like. These APIs include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compound include, but are not limited to, anecortive acetate; tetrahydrocortisol, 4,9(11)- pregnadien-17α,21-diol-3,20-dione and its -21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

Another useful drug that can be incorporated into the coatings of the invention is sodium 2-mercaptoethane sulfonate (Mesna). Mesna has been shown to diminish myofibroblast formation in animal studies of capsular contracture with breast implants [Ajmal et al. (2003) Plast. Reconstr. Surg. 112:1455-1461] and may thus act as an anti-fibrosis agent.

Procoagulants include, but are not limited to, zeolites, thrombin, and coagulation factor concentrates.

In some embodiments, the amount of API included in the coating ranges between about 0.3 to about 2.8 micrograms/cm$^2$. In other embodiments, the amount of API included in the coating ranges between about 0.6 to about 1.4 micrograms/cm$^2$. In yet other embodiments, the amount of API included in the coating ranges between about 0.85 to about 1.20 micrograms/cm$^2$. In yet further embodiments, the amount of API included in the coating ranges between about 0.90 to about 1.10 micrograms/cm$^2$.

In other embodiments, the amount of each of rifampin and minocyclin included in the coating ranges between about 0.6 to about 1.4 micrograms/cm$^2$. In yet other embodiments, the amount of each of rifampin and minocyclin included in the coating ranges between about 0.85 to about 1.20 micrograms/cm$^2$. In yet further embodiments, the amount of each of rifampin and minocyclin included in the coating ranges between about 0.90 to about 1.10 micrograms/cm$^2$.

In general, the coatings are designed to release one or more APIs over time. In some embodiments, the APIs are eluted over time in an area surrounding or adjacent to a TMD (such as, for example, within the device "pocket" or within 3 inches in all dimensions). In some embodiments, the API may be eluted for up to 30 days. In some embodiments, between about 40% and about 100% of the APIs are release over a period of at least about 30 hours. In other embodiments, 60% and about 100% of the APIs are release over a period of at least about 30 hours. In other embodiments, between about 65% and about 100% of the APIs are released over a period of at least about 36 hours. In other embodiments, 80% and about 100% of the APIs are release over a period of at least about 36 hours. In other embodiments, between about 60% and about 100% of the APIs are release over a period of at least about 48 hours. In other embodiments, 80% and about 100% of the APIs are release over a period of at least about 48 hours. In other embodiments, between about 60% and about 100% of the APIs are released over a period of at least about 60 hours.

In other embodiments, 80% and about 100% of the APIs are release over a period of at least about 60 hours.

In yet further embodiments, no more than about 60% of the APIs are released within about 24 hours. In even further embodiments, no more than about 90% of the APIs are released after about 60 hours. In one embodiment, no more than about 50% of the APIs are released within about 12 hours; between about 40% and about 90% are released between about 12 and about 24 hours; between about 60% and about 100% are released between about 24 and about 36 hours; between about 65% and about 100% are released between about 36 and about 48 hours; and between about 70% and about 100% are released between about 48 and about 60 hours.

In some embodiments, the coated devices may be used to prevent, treat or mitigate bacterial colonization or infections. In some embodiments, the coating comprises an antibacterial agent(s), such that the antimicrobial agent(s) may be eluted over time. In other embodiments, the coating comprises minocycline, rifampin, or a mixture of minocycline and rifampin. In other embodiments, the antibacterial agent is eluted over a period of at least 24 hours. In yet further embodiments, the cumulative release of antibacterial agent is at least about 30% over 24 hours. In yet further embodiments, the cumulative release of antimicrobial agent is at least about 40% over 24 hours. In yet other embodiments, the cumulative release of antimicrobial agent is at least about 50% over 24 hours. In yet further embodiments, at least about 80% of the antimicrobial agent is released after 3 days. Of course, these release rates may be varied by choosing different polymer coating compositions as recognized by those of skill in the art.

In one embodiment, a gel or mesh device can be configured to be used in the implantation of an implantable medical device that is a TMD or an IMD as enumerated herein. In such an embodiment, the coating of the gel or mesh device can include a pharmacokinetic profile of antibiotic configured to be released into the surrounding tissue adjacent to the TMD or IMD to reduce or prevent TMD or IMD infection. Such a pharmacokinetic profile of antibiotic release from the coating can define a spatial and temporal distribution of the antibiotic with respect to the implanted TMD or IMD, which can determine the clinical efficacy and safety of the implantable TMD or IMD. In some embodiments, the pharmacokinetic profile of antibiotic release adjacent to the implanted TMD or IMD can achieve an optimal efficacy and safety for TMD or IMD infection prophylaxis. The pharmacokinetic profile of in vivo antibiotic release from an implanted TMD or IMD designed to prevent or reduce TMD or IMD infections can be characterized by several features that can include, for example: (1) less than about 75% of the antibiotics can be released by the coating in the first about 24 hours after implantation of the TMD or IMD; (2) more than about 80% of the antibiotics can be released by the coating in the first about 48 hours after implantation of the TMD or IMD; (3) more than about 95% of the antibiotics can be released from the coating in the first seven days after implantation of the TMD or IMD; (4) no antibiotic is detectable in the systemic circulation at about 1 hour, about 24 hours, and about 72 hours after implantation of the TMD or IMD, with an assay that has a sensitivity of at least about 500 ng/ml; or (5) the antibiotic can achieve a level equal or exceeding the Minimum Inhibitory Concentration ("MIC") of the antibiotic for methicillin-resistant *Staphylococcus aureus* on both sides of the TMD or IMD for at least 48 hours after implantation of the TMD or IMD. In these embodiments, any antibiotic or antimicrobial compound(s) may be used. In particularly preferred embodiments, the antibiotic or antimicrobial compound is selected from the group consisting of rifampin, minocycline, and mixtures thereof.

The coatings of the present invention may comprise between about 1% and about 50% of one or more APIs by total weight of the coating. In some embodiments, the coatings of the present invention may comprise between about 5% and about 30% of one or more APIs by total weight of the coating. In other embodiments, the coatings of the present invention may comprise between about 6% and about 25% of one or more APIs by total weight of the coating.

In some embodiments, the API is eluted locally, such as within about 3 inches of the TMD in all directions or dimensions, preferably within about 2.5 inches in all directions; more preferably within about 2 inches in all directions.

Those of ordinary skill in the art will appreciate that any of the foregoing disclosed APIs can be used in combination or mixture in coatings of the present invention.

Example 1

Table 1 below, shows the cumulative release of rifampin and minocycline from three formulations (Formulation A, Formulation B, and Formulation C). The mesh device used here includes a fully resorbable terpolymer of glycolic acid 6-hydroxycaproic acid and 1-3 propanediol. The total weight of the drug would range from about 5 mg to about 50 mg for Rifampin and about 5 mg to about 20 mg for Minocycline HCl. This is to keep, it is believed, the maximum drug that can be released in about 1 day to a maximum of about ¹⁄₁₀ of the oral daily dose. This low dose is sufficient for the product to be efficacious, since the drug is delivered locally at the site of action. This results in high tissue concentrations, which are above the minimum inhibitory concentrations of common pathogens. In some embodiments, the amount of each of rifampin and minocyclin comprise from about 0.85 to about 1.20 micrograms/cm2.

TABLE 1

| Time | Cumulative Release (%) | | |
|---|---|---|---|
| (h) | FORMULATION A | FORMULATION B | FORMULATION C |
| 0 | 0 | 0 | 0 |
| 2 | 37 (30 to 40) | 81 | 18 |
| 4 | 58 (50 to 60) | 94 | 28 |
| 6 | 70 (65 to 75) | 96 | 38 |
| 8 | 81 (75 to 85) | 98 | 50 |
| 24 | 95 (>90) | 99 | 94 |

Example 2

Figure 3:
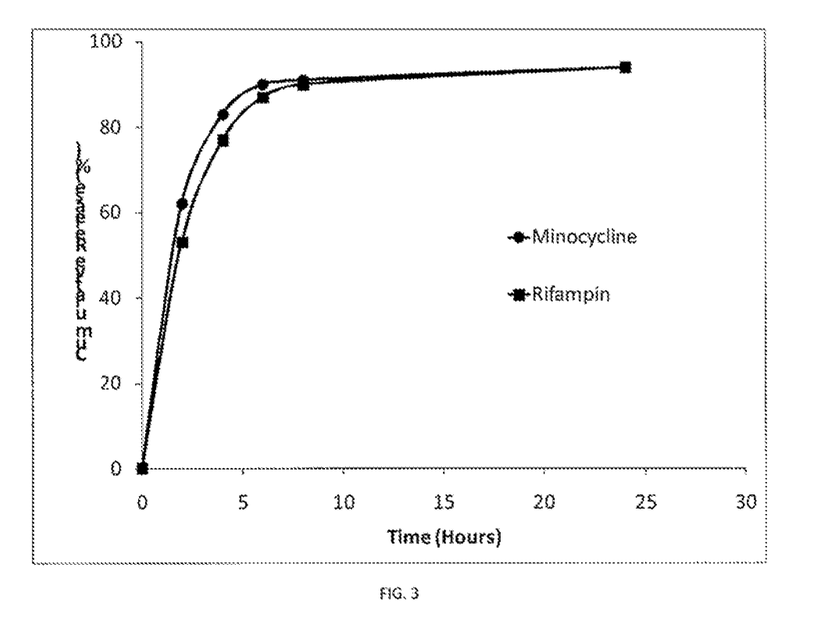
FIG. 3 depicts release profiles of active pharmaceutical ingredients from a coating of a mesh device in accordance with some embodiments of the present invention.

Table 2, shown below, shows tissue and pocket fluid levels of minocycline and rifampin for two lots for a mesh device having a coating including a mixture of tyrosine polyarylate, rifampin and minocycline. Further, cumulative release profiles of minocycline and rifampin for a mesh device having a coating including a mixture of tyrosine polyarylate, rifampin and minocycline are shown in FIG. 3.

TABLE 2

| | Tissue level after 24 h- (micrograms/mL) | | Pocket Fluid level after |  |
|---|---|---|---|---|
| Lot # | Rifampin | Minocycline | 24 h-(micrograms/mL) | |
| 11A31AR | 1.4 | 1.1 | 27.3 | 64.2 |
| NB172-25 | 4.9 | 9.6 | 40.1 | 64.4 |

Example 3

Standard in vitro studies were conducted to demonstrate effectiveness against several pathogenic organisms.

Minimum Inhibitory Concentrations

Establishing the MIC of antimicrobials is a necessary step in the process of establishing effective use concentrations. Approved standards for this activity with antibiotics are published by NCCLS. These standards are primarily intended for use in clinical settings with patient isolates. However, they represent a consensus methodology for best practice in determining MICs that are reproducible and defensible. The principles upon which they are based provide a sound framework for determining the MIC for the test.

Materials:

The broth dilution method was used to measure quantitatively the in vitro activity of an antimicrobial agent against a given microbial isolate. To perform the test, a series of tubes were prepared with a broth to which various concentrations of the antimicrobial agent were added. The tubes were then inoculated with a standardized suspension of the test organism. After incubation the tubes were examined and the minimal inhibitory concentration (MIC) was determined.

The following organism were used: *Acinetobacter baumanii* A TCC 19606; *Staphylococcus epidermidis* A TCC 14990; *Staphylococcus aureus* ATCC 6538; Methicillin-resistant *Staphylococcus aureus* ATCC 33591; *Escherichia coli* ATCC 8739; *Staphylococcus capitis* ATCC 35661; or *Staphylococcus schleiferi* ATCC 43808.

Results:

TABLE 3

| | Minimum Inhibitory Concentration (microgram/mL) | |
|---|---|---|
| Test Organism | Minocycline | Rifampin |
| S. aureus | 0.017 | 0.016 |
| S. epidermidis | 0.017 | 0.016 |
| E. coli | 2.233 | 2.057 |
| MRSA | 2.233 | 2.057 |
| A. baumanii | 0.140 | 0.129 |
| S. capitis | 0.017 | 0.016 |
| S. sclefeifreii | 0.017 | 0.016 |

The device is believed to be effective against each of these organisms.

Example 4

A mesh or gel (as described herein) is designed to deliver at least one API, including but not limited to one or more antimicrobial agents, anesthetics, procoagulant agents, and/or anti-inflammatory agents, to the area in and/or around the injection port (also known as the insufflation port or reservoir) of a laparoscopic adjustable gastric banding (LAGB) device. Previous work demonstrates that infections are associated with the injection port of a LAGB device (Facek, et al., ANZ J Surg 80 (2010) 506-509). The device would is anchored to the injection port and/or another part of the LAGB device and/or adjacent tissue and elute a fixed dose of at least one API, including but not limited to one or more antimicrobial agents, anesthetics, procoagulant agents, and/or anti-inflammatory agents, for a period of time in and/or around the injection port. The clinical purpose of this device would be determined by the drug that is released and could include analgesia, infection reduction, anti-coagulation, and improved host tolerance of the LAGB device.

Example 5

A mesh comprising an antimicrobial agent is anchored to the injection port of a LAGB. The mesh elutes antimicrobial agent over time to the tissue surrounding the injection port.

Example 6

A gel comprising an antimicrobial agent is deposited or injected in an area adjacent to the injection port of a LAGB. The gel is sufficiently viscous to remain in place over time as the antimicrobial agent is eluted to the tissue surrounding the injection port.

REFERENCES

Fabry, Hands, Obesity Surgery, "A Technique for Prevention of Port Complications after Laparoscopic Adjustable Silicone Gastric Banding," 12, 285-288.

Facek, Michael, "Prosthesis Related Sepsis Following Laparoscopic Adjustable Gastric Banding," ANZ J Surg, 80 (2010) 506-509.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system comprising:
an implanted transdermal medical device; and
a device comprising a mesh having at least one bioresorbable polymer coating, said coating comprising at least one active agent which is eluted over time, and said device being positioned in and around an injection port of the implanted transdermal medical device, wherein the implanted transdermal device is a gastric lap band.

2. The system of claim 1, wherein the device comprising the mesh is porous.

3. The system of claim 1, wherein the device comprising the mesh is formed from knitted, braided, woven or non-woven fibers.

4. The system of claim 1, wherein the mesh is formed of at least one bioresorbable polymer.

5. The system of claim 1, wherein the at least one bioresorbable polymer coating comprises a tyrosine-derived polyesteramide.

6. The system of claim 5, wherein the tyrosine-derived polyesteramide is a member of the P22 family of tyrosine-derived polyesteramides.

7. The system of claim 6, wherein a percentage of free acid in the P22 family of tyrosine-derived polyesteramides ranges from about 5% to about 40%.

8. The system of claim 6, wherein a percentage of free acid in the P22 family of tyrosine-derived polyesteramide is about 27.5%.

9. The system of claim 1, wherein the coating comprises a tyrosine-derived polyesteramide and at least one polymer selected from the group consisting of polylactic acid, polyglycolic acid, poly(L-lactide) (PLLA), poly(D,L-lactide) (PLA) polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, polyethyl glutamate-co-glutamic acid), poly(tert-butyloxy-carbonylmethyl glutamate), poly-caprolactone (PCL), polycaprolactone co-butylacrylate, polyhydroxybutyrate (PHBT), polyhydroxybutyrate, poly (phosphazene), poly(phosphate ester), poly(amino acid), polydepsipeptides, polyiminocarbonates, poly[(97.5% dimethyl-trimethylene carbonate)-co-(2.5% trimethylene carbonate)], poly(orthoesters), tyrosine-derived polycarbonates, tyrosine-derived polyiminocarbonates, tyrosine-derived polyphosphonates, polyethylene oxide, polyalkylene oxides, and hydroxypropylmethylcellulose.

10. The system of claim 1, wherein the active agent is an antimicrobial agent, an anesthetic, a procoagulant agent, or an anti-inflamatory agent.

11. The system of claim 10, wherein the antimicrobial agent is selected from the group consisting of antibiotics, antiseptics, and disinfectants.

12. The system of claim 11, wherein the antibiotic is selected from the group consisting of tetracyclines, penicillins, macrolides, rifampin and combinations thereof.

13. The system of claim 12, wherein the antibiotic comprises a combination of minocycline and rifampin.

14. The system of claim 1, wherein said active agent is released from said coating over about a 24 hour time period.

15. The system of claim 1, wherein said active agent is released from said coating over about a 48 hour time period.

16. The system of claim 1, wherein said active agent is released from said coating over about a 120 hour time period.

17. The system of claim 1, wherein said active agent is rifampin, minocycline, or a mixture thereof and wherein at least about 60% of said rifampin, minocycline, or a mixture thereof is released within about 24 to about 36 hours.

18. The system of claim 1, wherein said active agent is minocycline and a tissue concentration of said minocycline is selected from the group consisting of between about 0.65 µg/mL and 0.8 µg/mL after about 2 hours, about 2.55 µg/mL and about 2.75 µg/mL after about 6 hours, and about 1.2 µg/mL and about 1.9 µg/mL after about 24 hours.

19. The system of claim 1, wherein said active agent is minocycline and a tissue concentration of said minocycline is between about 0.65 µg/mL and about 0.8 µg/mL after about 2 hours; where the tissue concentration of said minocycline is between about 2.55 µg/mL and about 2.75 µg/mL after about 6 hours; and where the tissue concentration of said minocycline is between about 1.2 µg/mL and about 1.9 µg/mL after about 24 hours.

20. The system of claim 1, wherein said active agent is rifampin and a tissue concentration of said rifampin is selected from the group consisting of between about 0.6 µg/mL and 1.4 µg/mL after about 2 hours, about 1.9 µg/mL and about 2.3 µg/mL after about 6 hours, and about 2.6 µg/mL and about 4.2 µg/mL after about 24 hours.

21. The system of claim 1, wherein said active agent is rifampin and a tissue concentration of said rifampin is between about 0.6 µg/mL and 1.4 µg/mL after about 2 hours; where the tissue concentration of said rifampin is between about 1.9 µg/mL and about 2.3 µg/mL after about 6 hours; and where the tissue concentration of said rifampin is between about 2.6 µg/mL and about 4.2 µg/mL after about 24 hours.

22. The system of claim 1, wherein said active agent achieves a level equal or exceeding a minimum inhibitory concentration of said active agent for methicillin-resistant *Staphylococcus aureus* on both sides of said implanted transdermal medical device for at least about 24 hours after implantation of said implanted transdermal medical device.

23. The system of claim 1, wherein said active agent achieves a level equal or exceeding a minimum inhibitory concentration of said active agent for methicillin-resistant *Staphylococcus aureus* on both sides of said implanted transdermal medical device for at least about 48 hours after implantation of said implanted transdermal medical device.

24. The system of claim 1, wherein the mesh prevents tissue in-growth from a tissue surrounding the implanted transdermal device.

25. A system comprising:
a gastric lap band; and
a composition comprising at least one bioresorbable polymer, the composition comprising rifampin and minocycline which is eluted over time, the composition being positioned in and around an injection port of the gastric lap band.

26. The system of claim 25, wherein the composition is a formulation selected from the group consisting of a putty, a paste, a gel, a foam, an ointment, and a cream.

27. The system of claim 25, wherein an amount of the at least one bioresorbable polymer ranges from about 30% to about 80% by weight of the composition.

28. The system of claim 25, wherein the at least one bioresorbable polymer is a tyrosine-derived polyesteramide.

29. A method of reducing infection in tissue surrounding a gastric lap band, the method comprising: eluting an active agent from a composition or device wherein the device comprises a mesh having at least one bioresorbable polymer coating, wherein the active agent is eluted from the composition or the coating over time and the composition or device is positioned in and around an injection port of the gastric lap band.

30. The method of claim 29, wherein the active agent is an antimicrobial agent, an anesthetic, a procoagulant agent, or an anti-inflamatory agent.

* * * * *